United States Patent [19]
Goldsmith

[11] Patent Number: 5,306,466
[45] Date of Patent: Apr. 26, 1994

[54] DETECTION OF CONTAMINANTS IN FOOD

[75] Inventor: Robert M. Goldsmith, Pasadena, Calif.

[73] Assignee: California South Pacific Investors, Pasadena, Calif.

[21] Appl. No.: 64,521

[22] Filed: May 19, 1993

[51] Int. Cl.<sup>5</sup> ............................................. G01N 21/00
[52] U.S. Cl. ........................................ 422/58; 422/61; 436/1; 436/164; 426/232; 116/206
[58] Field of Search ................. 422/56, 58, 61; 436/1, 436/164; 426/232; 116/206

[56] References Cited

U.S. PATENT DOCUMENTS

| 2,485,566 | 10/1949 | Clark | 426/232 |
| 3,067,015 | 1/1960 | Lawdermilt | 422/58 |
| 5,053,339 | 10/1991 | Patel | 422/58 |

Primary Examiner—Lyle A. Alexander
Attorney, Agent, or Firm—Christie, Parker & Hale

[57] ABSTRACT

A food contamination detector. The detector comprises a tray for holding a food product. A collector is placed in the tray for collecting liquids from the food. A bar code detector is located in the collector.

19 Claims, 3 Drawing Sheets

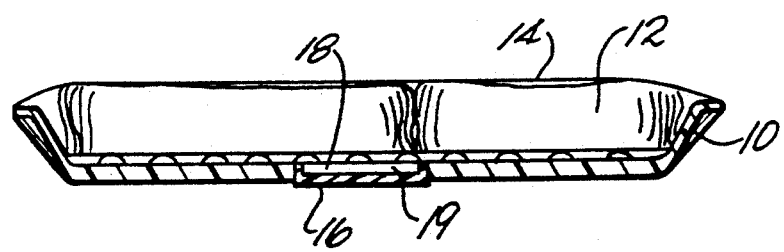
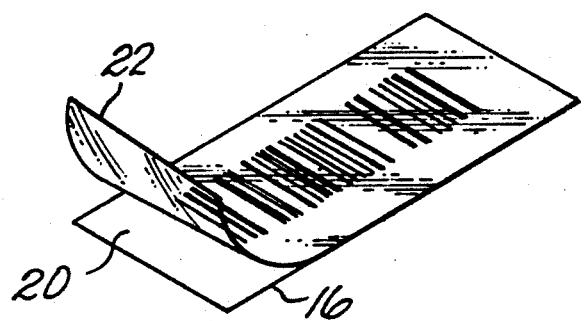

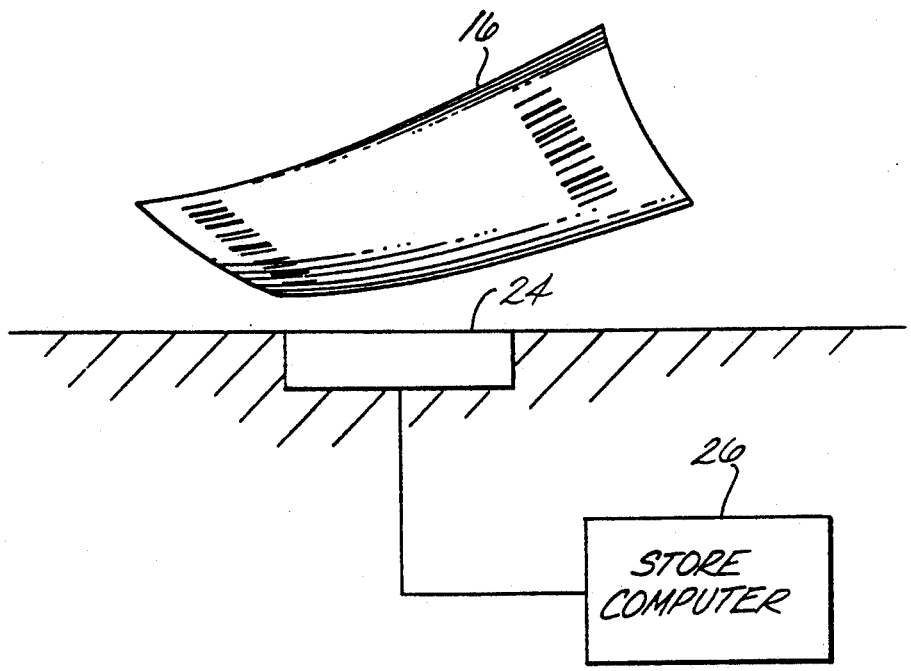

DETECTION OF CONTAMINANTS IN FOOD

FIELD OF THE INVENTION

The present invention relates to detecting the presence of toxic contaminants in food.

BACKGROUND OF THE INVENTION

Over the past several years there has been increasing concern over the safety of our food supply. Contamination of food can come from a variety of sources and the type of contamination possible is often dependent on the food involved.

Most animal derived food products, such as raw meat, are exposed to the possibility of contamination during processing. Such contamination comes from, for example, contact with faecal matter at the slaughter house, from handlers of the food products at any stage of the processing of the food products or from toxins, both naturally occurring and man-made, present in the environment where the food was grown or processed. In most cases, contamination is minor and, if the food is prepared properly, is not a serious threat to the consumer. However, while the contamination of food is generally low, i.e. few bacteria per gram of the food, if the food is not stored under satisfactory conditions or stored for long periods of time, contaminants, such as bacteria, grow to be become a serious threat to the eventual consumer of the products. Even if the food products reach the market in an acceptable condition, subsequent treatment by the consumer may lead to the development of serious contamination of the food.

A number of incidents and factors have lead to the growing concern of the food supply. These include:
- raw chicken and egg products have been found to be contaminated with Salmonella and inadequate cooking of such products has led to serious illness or death of persons who have consumed the contaminated products;
- mild products which have been inadequately pasteurized have been found to be contaminated with Listeria which has lead to serious illness or death of consumers of the products;
- a highly toxic strain of E. coli has lead to the death of several people who consumed prepared foods which had been inadequately cooked;
- a number of toxins are known, such as ciguatoxins, which contaminated fish. These toxins are not killed by cooking and so their presence in fish is a threat to any consumer of the product;
- shell fish, such as oysters, concentrate any contaminants present in the water in which they grow and, since they are frequently eaten raw, pose a threat to the health of consumers; and
- fish is increasingly eaten raw which adds to the possibility of increased outbreak of illness with water borne contaminants.

The only means the consumer has of determining if the food they purchase is contaminated is by visual inspection and by smell. These are usually inadequate to detect contamination.

There is a need for a reliable way to detect if a food product purchased by a consumer is fit for consumption. Any solution to this problem should be relatively inexpensive and able to detect a number of agents capable of causing illness. It should also be simple to "read" so that a consumer, who does not have access to sophisticated testing equipment or specialized knowledge, can readily determine if the products they have purchased are free from contamination.

SUMMARY OF THE INVENTION

A food contamination detector is described. The detector comprises a tray, for holding a food product, which is provided with a collector for collecting liquids from the food. A bar code detector means is located in the collector. In one embodiment the bar code detector comprises a toxin printed onto a substrate and an indicator bound to the toxin to form a bar code. When the bar code detector is contacted with a toxin, the indicator is removed from the substrate destroying the bar code. In use the destruction of the bar code is discernible by visual inspection of the bar code or by an electronic scanner.

BRIEF DESCRIPTION OF THE DRAWINGS

These and other features and advantages of the present invention will be better understood by reference to the following detailed description when considered in conjunction with the accompanying drawings in which:

FIG. 3 is a side sectional view of the bar code detector system in the package; and FIG. 4 shows a bar code, of one embodiment of the present invention, prior to attachment to a food package.

FIG. 5 shows a bar code scanner for use in the present invention.

DETAILED DESCRIPTION

The present invention uses the same bar code that identifies the product at point of purchase as a detector system for toxins and other contaminants that may be present in food products.

Figure 1:
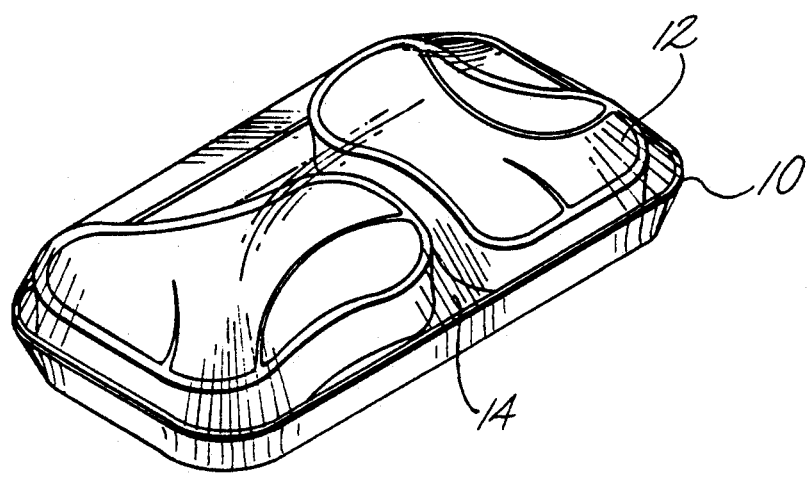
FIG. 1 is a top view of a packaged food product.
Figure 2:
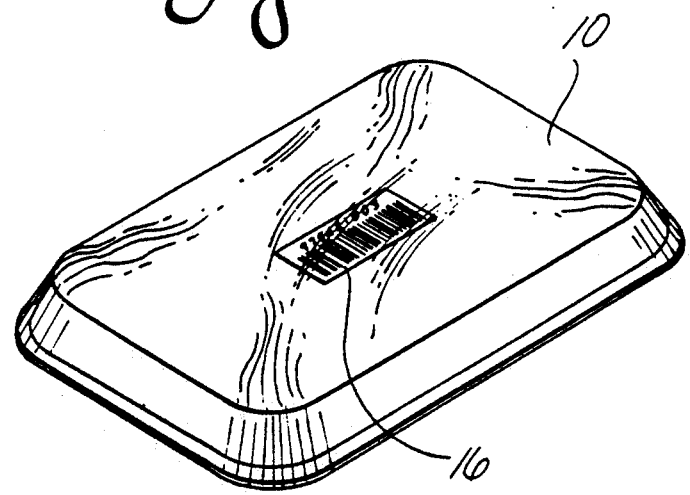
FIG. 2 is a bottom view of a packaged food product showing a bar code detector system.

Food products are often "mass produced" and sold at retail outlets in prepackaged containers such as that illustrated in FIGS. 1-3. Typically, such packages include a tray 10 which contains the food product 12. The tray and food are sealed in a plastic wrap material 14. Bar codes 16 are used on the products for scanning at the check-out register (see FIG. 5), to reduce errors in totaling purchases and for stock control. The bar code comprises a series of bars which represent a number identifying the product.

In the practice of the present invention the bar code also serves the purpose of detecting toxins in the food products.

In one embodiment of the present invention the bar code 16 is attached to, covers and seals a hole 18 in the exterior of the bottom of the tray (see FIG. 3). The hole allows liquids and juices from the food to come in contact with and collect above the bar code, thus forming a collector 19 for the liquids and juices.

In one embodiment of the present invention the bar code is printed on a transparent membrane 20. The membrane is self-adhesive for attachment to the food tray. Such bar codes can be prepared with a peelable, protective material 22 (see FIG. 4).

In one embodiment of the present invention the "bar codes" are formed by labeled antibodies bound to antigens which are "printed" in a bar code pattern on the transparent membrane 20.

"Bar codes" are prepared by irreversibly binding an antigenic determinant of toxins or contaminants of interest to the transparent membrane. The antigenic determinant may be a small portion of the toxin, which is specific for that toxin, it may be the toxin itself, an analog of the toxin or other compound which is capable of "mimicking" the toxin, or pathogenic microorganisms, all of which are referred to herein as "toxins." Membranes suitable for binding the toxin are well known in the art and include membranes such as those made from activated hydrophobic polyvinylidene, polyvinylidene difluoride, mixed esters of cellulose nitrate and cellulose acetate, hydrophobic polyvinylidene difluoride, hydrophilic polyvinylidene difluoride, laminated and unlaminated polytetrafluroethylene, microfiber glass, cellulose and polypropylene. Once toxins are bound to the membrane other binding sites, which remain on the membrane, are blocked by contacting them with an "inert" binding agent such as bovine serum albumin or other suitable blocking agent.

Once the toxin is bound to the membrane a labeled antibody, which exhibits a specificity for the toxin, is bound to the toxin. Antibodies suitable for use in the present invention include monoclonal and polyclonal antibodies. The preparation of such antibodies, specific for a desired toxin, are well known in the art. In some cases it may be necessary to conjugate the toxin to a protein to "mask" the toxicity of the antigen. Otherwise injection of the toxic antigen may result in the death of the animal in which the antibodies are to be prepared. Methods of conjugating compounds are well known in the art and one such method is described by Hokama et al., Mycotoxins and Phycotoxins '88, A Collection of Invited Papers at the Seventh International IUPAC Symposium of Mycotoxins and Phycotoxins, Toyko, Japan 1988, pp. 303–310 (Elsevier Science Publishers, Amsterdam), which is incorporated herein by reference.

In one embodiment of the present invention the antibody is labeled with a colored latex bead. The preparation of antibodies labeled with colored latex beads is well known in the art. Such labeled antibodies may be prepared by diluting latex beads in a solution such as phosphate-buffered saline (8.1 mM $Na_2HPO_4$, 1.5 mM $KH_2PO_4$, 137 mM NaCl, 1.6 mM KCl) and mixing the solution gently to suspend and distribute the latex beads in the solution. Preferably, about a 10% (wt/v) suspension of latex beads is diluted about 1:100, to give a suspension of about 0.1% (wt/v) latex beads. An antibody solution is added to the latex bead suspension. Preferably, about 0.3 to about 0.6 mg of antibodies are added for each mg of latex beads, however, this ratio will vary depending on the specificity and sensitivity of the antibody preparation and the type of support being used. The amount of antibody to be used for the preparation of labeled antibodies is derived experimentally, using different dilutions of the antibody preparation. After addition of the antibody, the solution is gently mixed and incubated at about 4° C. for about 16 to about 20 hours. At the completion of the incubation, the labeled antibodies are washed with phosphate-buffered saline, and the sensitivity and specificity of the labeled antibody preparation are tested.

The sensitivity and specificity of the labeled antibodies are tested by coating a membrane with a preselected amount of toxin. When contacted with the labeled antibody, the labeled antibody bind to the toxin, resulting in the development of the desired color on the membrane. The color which develops will not be washed off by rinsing in a solution such as phosphate-buffered saline. Binding of the antibody to the toxin results in the development of color for the bar code design forming a bar code detector system, i.e. the labeled antibodies act as a type of "ink" so the bar code symbol can be visualized.

In use with raw meat products, the bar code detector is placed in contact with juices from the meat. This can be achieved by placing bar code 16 in the bottom of and covering hole 18 in meat tray 10 forming collector 19, as shown in FIGS. 1–3. The juices collect in the collector and come in contact with the bar code. If a toxin is present in the juices the antibodies will release from the bar code design and bind to the toxins present in the juices, thus destroying the bar code design. Such antibody type assays are well known in the art and are referred to as competition assays. A consumer can detect the presence of the toxin in the food product by a visual inspection of the bar code. If the consumer does not notice the abnormality in the bar code, it will be detected by the bar code scanner 24 at the check-out counter (see FIG. 5). A store computer 26, connected to the scanner, would emit an alarm to warn that a defective bar code has been detected. The contaminated products can then be replaced with non-contaminated products.

A labeled antibody is one means of indicating the presence of a toxin in the juices of a food product. Those skilled in the art will be aware of other indicators such as chemical indicators, which are useful in the practice of the present invention.

The bar code scanner also indicates that products, at the time they left the supplier, were in satisfactory condition. If contaminated products are detected the supplier can gain an indication of the source of contamination and implement remedial steps to ensure that the source of contamination is eliminated.

The toxins printed into the membrane to form the bar code could be the same for all the bars imprinted or each bar could be a different toxin. In this way a number of contaminants or toxins, that are commonly associated with a particular food, can be detected. The bar code would not only indicate that the food was contaminated but would also indicate the type of contamination.

Accordingly, the foregoing description should not be read as pertaining only to the precise structure, as described and shown in the accompanying drawings, but rather should be read consistent with and as support to the following claims which have their fullest and fair scope.

What is claimed is:

1. A food contamination detector for identifying the presence of toxins in food comprising:
    a toxin printed onto a substrate; and
    an indicator bound to the toxin to form a bar code on the substrate such that when the detector is contacted with a toxin, specific for the indicator, the indicator is removed from the substrate, destroying the bar code and thereby indicating the presence of the toxin in the food.

2. A food contamination detector as recited in claim 1 wherein the toxins are selected from the group consisting of Salmonella sp., Listeria Sp., E. coli, ciguatoxin and related marine polyethers, domoic acid and aflatoxin.

3. A food contamination detector as recited in claim 1 wherein the substrate comprises a transparent membrane.

4. A food contamination detector as recited in claim 1 wherein the indicator comprises an antibody bound to a latex bead.

5. A food contamination detector as recited in claim 4 wherein the antibody is selected from the group consisting of monoclonal antibodies and polyclonal antibodies.

6. A food contamination detector for identifying the presence of toxins in food comprising:
   a first toxin printed onto a substrate at a first position;
   a second toxin printed onto a substrate at a second position;
   a first indicator bound to the first toxin;
   a second indicator bound to the second toxin such that the first and second indicators form parallel bars on the substrate which can be detected by an optical scanner and where the presence of a food sample containing a contaminant specific for the indicators will cause the indicator to become unbound and efface the parallel bar pattern to thereby indicate the food is contaminated.

7. A food contamination detector as recited in claim 6 wherein the toxins are selected from the group consisting of Salmonella sp., Listeria Sp., *E. coli*, ciguatoxin and related marine polyethers, domoic acid and aflatoxin.

8. A food contamination detector as recited in claim 6 wherein the substrate comprises a transparent membrane.

9. A food contamination detector as recited in claim 6 where additional toxins are printed on the substrate and bound to indicators to form a bar code.

10. A food contamination detector as recited in claim 6 wherein the indicator comprises an antibody bound to a latex bead.

11. A food contamination device as recited in claim 10 wherein the antibody is selected from the group consisting of monoclonal antibodies and polyclonal antibodies.

12. A food contamination detector for identifying the presence of toxins in food comprising:
   a tray for holding a food product;
   a collector in the tray for collecting liquids from the food product; and
   a bar code detector located in the collector wherein the bar code detector comprises:
   a toxin printed on a substrate in a bar code pattern; and
   an indicator bound to the toxin to make the bar code pattern visible.

13. A food contamination detector as recited in claim 12 wherein the toxins are selected from the group consisting of Salmonella sp., Listeria Sp., *E. coli*, ciguatoxin and related marine polyethers, domoic acid and aflatoxin.

14. A food contamination detector as recited in claim 12 wherein the substrate comprises a transparent membrane.

15. A method of detecting contaminants in food comprising:
   printing toxins onto a substrate;
   binding an indicator to the toxins to form a bar code detectable by an optical scanner;
   contacting the bar code with material derived from the food which is suspected of being contaminated with a toxin; and
   scanning the bar code to thereby detect the presence of contaminants in the food.

16. A method as recited in claim 15 wherein the toxins are selected from the group consisting of Salmonella sp., Listeria Sp., *E. coli*, ciguatoxin and related marine polyethers, domoic acid and aflatoxin.

17. A method as recited in claim 15 wherein the substrate comprises a transparent membrane.

18. A method as recited in claim 15 wherein the indicator comprises an antibody bound to a latex bead.

19. A method as recited in claim 18 wherein the antibody is selected from the group consisting of monoclonal antibodies and polyclonal antibodies.

* * * * *

UNITED STATES PATENT AND TRADEMARK OFFICE
Certificate

Patent No. 5,306,466                                          Patented: April 26, 1994

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Robert M. Goldsmith; Catherine H. Goldsmith; and James Gilbert Woodaman.

Signed and Sealed this First Day of August, 2000.

JILL WARDEN
*Supervisory Patent Examiner*
Art Unit 1743